US005571976A

United States Patent [19]
Drolet

[11] Patent Number: 5,571,976
[45] Date of Patent: Nov. 5, 1996

[54] APPARATUS AND METHOD FOR COLLECTING SAMPLES FOR IMS (ION MOBILITY SPECTROMETERS) ANALYZERS AND THE LIKE

[75] Inventor: Gerald Drolet, Ottawa, Canada

[73] Assignee: Her Majesty the Queen in right of Canada, as represented by the Minister of National Revenue, Nepean, Canada

[21] Appl. No.: 352,486

[22] Filed: Dec. 9, 1994

[51] Int. Cl.$^6$ .............................. G01N 1/08; G01N 1/02
[52] U.S. Cl. ........................................ 73/864.71; 73/864
[58] Field of Search ................................. 73/864, 864.71

[56] References Cited

U.S. PATENT DOCUMENTS

| | | | |
|---|---|---|---|
| 3,074,276 | 1/1963 | Moos | 73/864.71 |
| 4,405,430 | 9/1983 | Hanulik | 73/864 X |
| 4,580,440 | 4/1986 | Reid et al. | 73/864 X |
| 4,805,468 | 2/1989 | Choudry | 73/864.71 |
| 5,373,748 | 12/1994 | Lioy et al. | 73/864.71 |
| 5,443,271 | 8/1995 | Holsen et al. | 73/864.71 X |

FOREIGN PATENT DOCUMENTS

| 163339 | 7/1991 | Japan | 73/864.71 |
|---|---|---|---|

OTHER PUBLICATIONS

Graseby Security—"NARCOTEC" dated Aug. 1, 1993, 1 page.

Article by D. Smith et al from the Contraband and Cargo Inspection Technology International Symposium—"A Field Evaluation Of Drug Detection Technologies: Laboratory Confirmation of Drug Residues" dated Oct. 28–30, 1992; pp. 65–66, (article incomplete).

Article by Kim et al from the International Symposium of Forensic Science, Tokyo, entitled "Field Detection Of Illicit Drugs . . . Using Ion Mobility Spectroscopy"; Oct. 21–22, 1993, 7 pages.

Primary Examiner—Thomas P. Noland
Attorney, Agent, or Firm—Bereskin & Parr

[57] ABSTRACT

To facilitate collection of sample, for analysis in an ion mobility spectrometer or the like, a collection device is provided which can be mounted on the fingers, for example two fingers, of a user's hand. The collection device is formed of top and bottom layers of a sheet material, which are secured together along three sides and open end along a fourth side, to enable the user's fingers to be inserted. Mounted on a user's fingers, the device is run over surfaces of interest to collect a sample. It is then placed in a frame holder, and then inserted into an inlet station of an analysis device. There, any substances of interest are caused to pass into the analysis device for a reading to be taken.

6 Claims, 3 Drawing Sheets

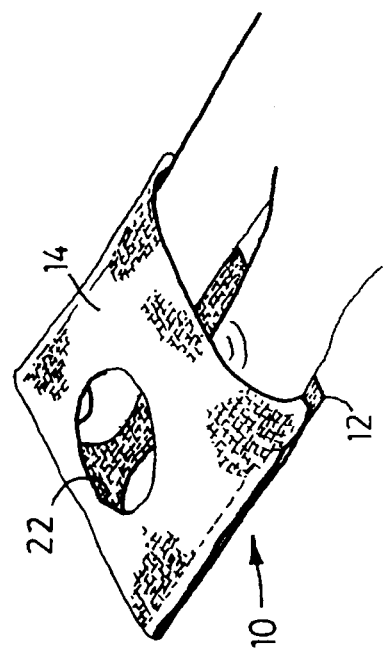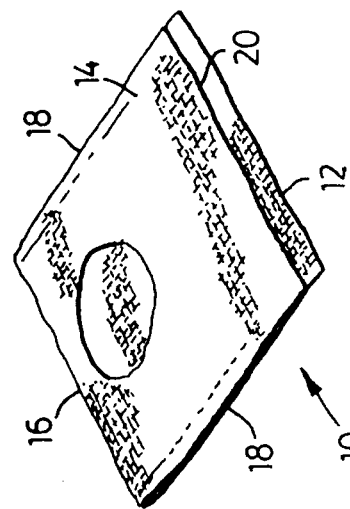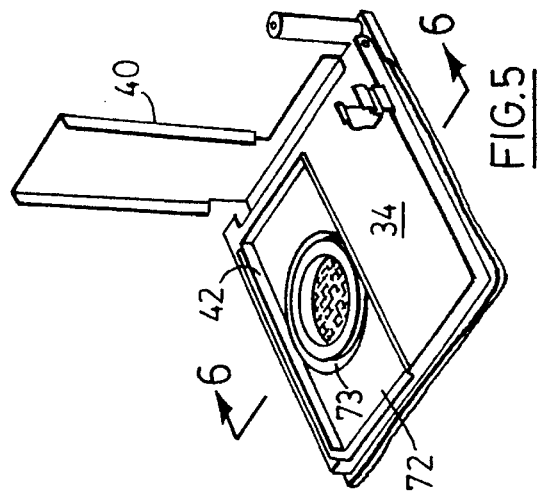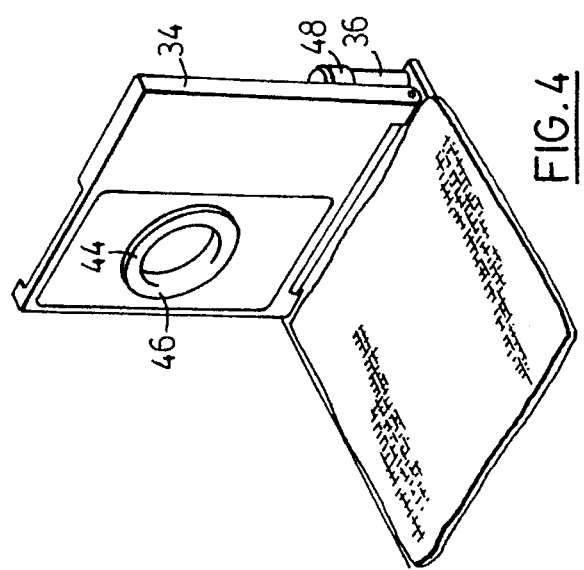

APPARATUS AND METHOD FOR COLLECTING SAMPLES FOR IMS (ION MOBILITY SPECTROMETERS) ANALYZERS AND THE LIKE

FIELD OF THE INVENTION

This invention relates to the collection of samples for analysis. This invention is more particularly concerned with the collection of samples of material that may be present in trace quantities only, for analysis in an Ion Mobility Spectrometer (IMS) or other device capable of detecting very low concentrations, eg in the nanogram and picogram range.

BACKGROUND OF THE INVENTION

IMS and other devices are being increasingly used to detect trace quantities of substances. For example, at airports and the like, there is commonly a strong demand for detection of explosives, illegal narcotics and other substances. In the past, the lack of suitable machines or devices for detecting such substances has lead to use of trained dogs for detecting them. This has its own disadvantages. Clearly, a dog can only work for a certain length of time and a dog's degree of enthusiasm and interest can vary.

More recently, IMS devices have become available having an extremely high degree of sensitivity, sufficient to detect very low levels of narcotics and the like. They are sufficiently sensitive that even minute quantities of these substances, in the nanogram or picogram range, left on the exterior packages, suitcases etc. can be detected.

However, if the substances are to be detected, there is a fundamental problem of collecting a sample for insertion into an IMS device. A common current technique is to use a small hand-held vacuum cleaner with a teflon filter. This is run over a suitcase or other object of interest. The filter is then removed and inserted into the IMS device and subject to heating leading to vaporization and desorption of vapors of interest.

This technique has numerous disadvantages. It is relatively time consuming and complicated. The vacuum cleaner is noisy and intrusive. In the nature of such an investigation, in a crowded airport for example, it is desirable to be able to gather a sample unobtrusively and discreetly. Further, vacuum samplers require batteries, so they are large and cumbersome.

It requires the filter to be manually removed from the vacuum cleaner and inserted into the IMS device. More significantly, if a "hit" is obtained, i.e. if one of certain substances is detected, then this requires that the various items of equipment used be carefully cleaned. The reason for this is that possibly some trace particles or condensed vapors remain adhered inside the inlet to the vacuum cleaner. If these are not removed, they could become dislodged and then embedded on the filter to give a false positive reading for a later test. It is therefore necessary to carefully clean the vacuum cleaner and other components. This is exceedingly inconvenient, and results in considerable operational delay and inconvenience.

Other techniques have been suggested, but these still have numerous disadvantages. For example, it is known to use a glove, in which case a user's hand is simply run over the suitcase or object of interest. The glove itself is then vacuumed, which is an additional step. Again this leads to the same problem of contamination of the vacuum cleaner if a positive sample is found.

It has been proposed to use a light stainless steel mesh in a holder. While this can be held in a machine, it is too inflexible, and is generally not effective.

Accordingly, it is desirable to provide some method of collecting samples for analysis in an IMS device or the like, which is cheap, simple and effective. Further, the collection technique should not require any significant down time or cleaning to be required if and when a positive indication is found for substances of interest.

SUMMARY OF THE PRESENT INVENTION

In accordance with the present invention, there is provided a collection device for use in collecting a sample for analysis, the collection device being flexible and generally sheet-form and comprising top and bottom layers of a flexible material, and means securing the top and bottom layers together around substantially three sides thereof, with a fourth side of the collection device being open for insertion of a user's fingers. Both of the top and bottom layers are generally rectangular and are secured together along the sides and rear edges thereof, with the device being open along a front edge thereof. Additionally, the bottom layer extends beyond the top layer along the front edge.

BRIEF DESCRIPTION OF THE DRAWING FIGURES

For a better understanding of the present invention and to show more clearly how it may be carried into effect, reference will now be made, by way of example, to the accompanying drawings, which show a preferred embodiment of the present invention and in which:

FIG. 1 is a perspective view of a collection device according to the present invention;

FIG. 2 is a perspective view of a collection device of FIG. 1, in use, on a user's fingers;

FIG. 3 is a perspective view of a holding frame, for the collection device of FIGS. 1 and 2;

FIG. 4 is a perspective view of the collection device of FIGS. 1 and 2, located on a holding frame, shown in an open configuration;

FIG. 5 shows the collection device in the holding frame of FIG. 3, in a closed position;

Figure 6A:
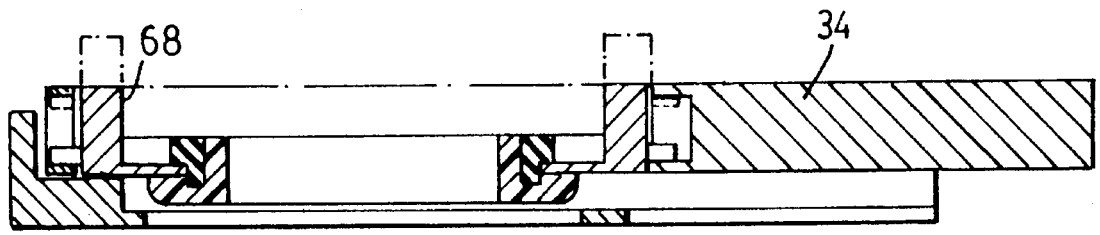
Figure 6B:
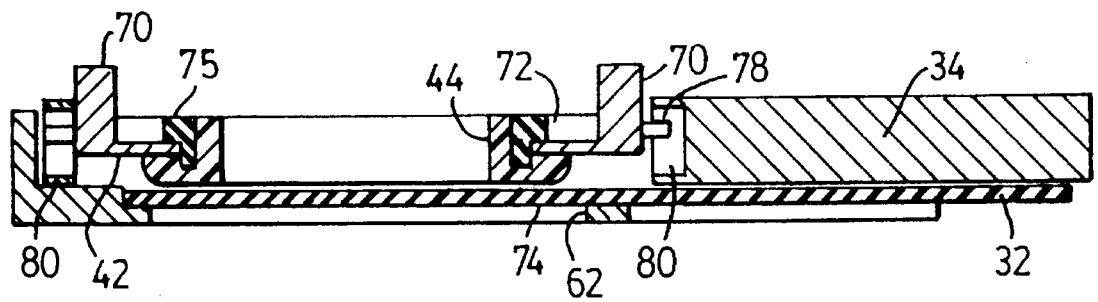
Figure 7:
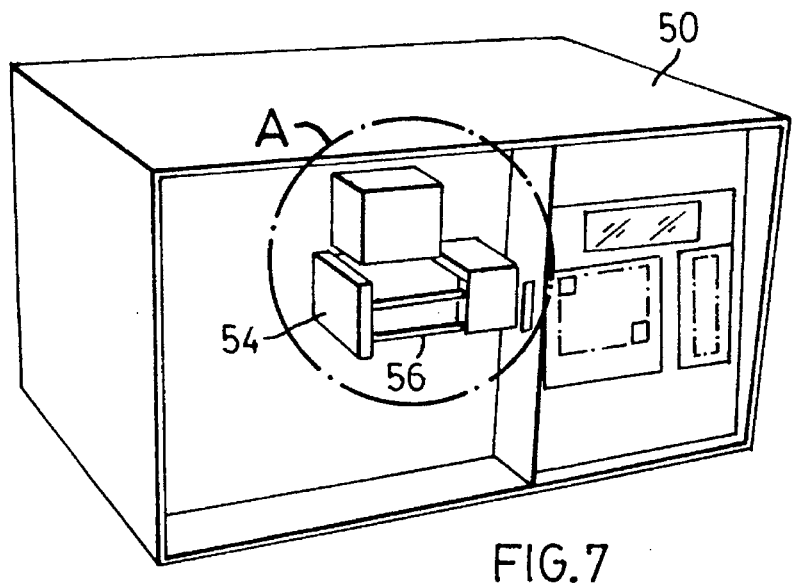

FIGS. 6(a) and 6(b) are sectional views along line 6—6 of FIG. 5;

FIG. 7 is a perspective view of a conventional IMS device; and

Figure 8A:
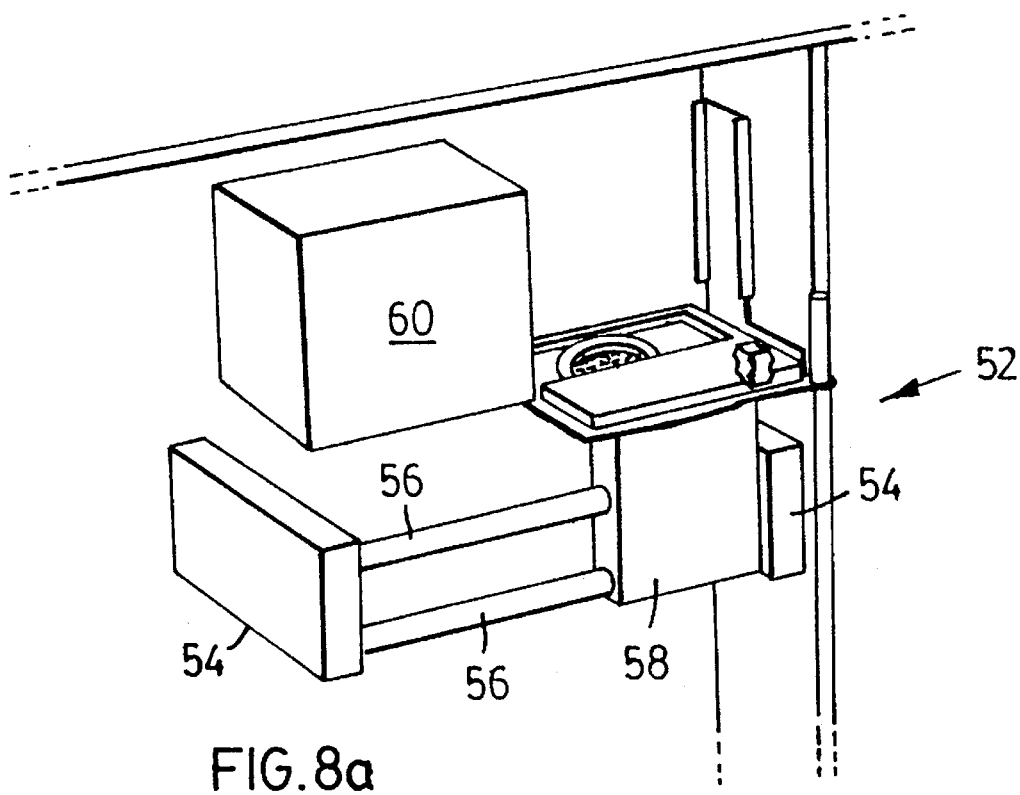
Figure 8B:
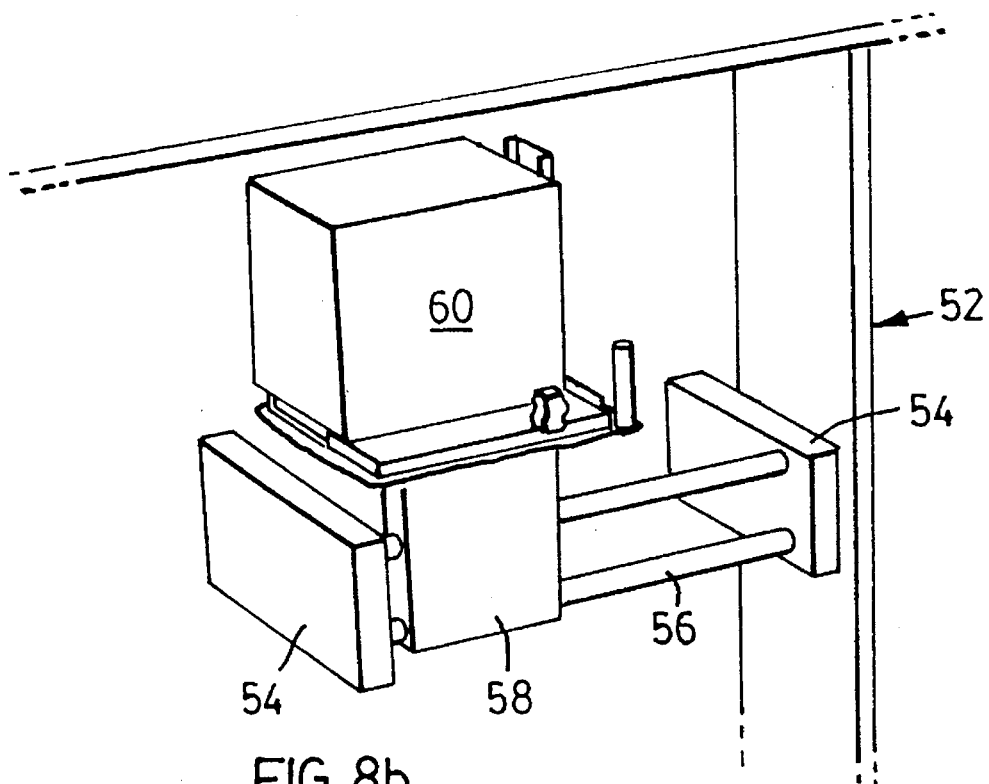

FIGS. 8(a) and 8(b) shows detail A of FIG. 7 on an enlarged scale, and insertion of the mounting frame into the IMS device.

DESCRIPTION OF THE PREFERRED EMBODIMENTS

Referring to FIGS. 1 and 2, a collection device according to the present invention is generally indicated by the reference 10. The collection device 10 has the configuration of a generally square, small bag. The collection device 10 has a bottom layer 12 which is continuous and is intended for collection of a sample. As such, the bottom layer 12 should be formed from a relatively fine mesh material, here 100% cotton. Any suitable cotton can be used. It has been found that sizing material used on cotton can have a contaminating effect, giving corrupted readings, so the cotton is preferably untreated or coated.

To complete the bag, a top layer 14 is provided.

In this embodiment, for simplicity, the top layer 12 and 14 are continuous with one another, along a rear edge 16. Along either side edge 18, the top and bottom layers 12, 14 are sewn together, so that the collection device is open only along a front edge 20. Sewing is preferred to gluing, since many glues or adhesives can give off vapors, which can result in false readings. For rome applications staples or the like may be suitable.

As will be explained in greater detail below, the main function of the top layer 14 is to enable the collection device 10 to be secured onto a users fingers. In this embodiment, the top layer 14 is provided with a circular aperture 22 to facilitate desorption of sample vapors from a sample adhered to a bottom layer 12. With this in mind, it will be appreciated that the top layer 14 need not be a continuous, fine mesh type of material as for the bottom layer 12. Rather, the top layer 14 could be an open-mesh material, showing relatively large openings. Provided the top layer 14 is, in general terms, sufficiently continuous to cover a user's fingertips, it will serve the function detailed below. It is also expected that a open mesh structure would further facilitate desorption of sample vapors, and may render the provision of the aperture 22 unnecessary.

It can be noted that the bottom layer 12 is slightly longer than the top layer 14 at the front, again to facilitate insertion of user's fingers. Preferred dimensions for the top and bottom layers are 3¼" wide with the bottom layer 12 being approximately 3" long from front to back and the top layer 14 being 2¾" long from front to back. The circular aperture 22 has a diameter of approximately 1⅛" centred equally from either side edge 18 and approximately ⅞" from the rear edge 16.

In use, as shown in FIG. 2, a user can slip two fingers into the bag or collection 10, conveniently the index and middle fingers. The two fingers can then be held apart against the side edges, to maintain the layers 12, 10 generally in tension but still flexible. The bag or collection device 10 is then retained on the fingers by friction.

The device 10 can then be run over the edges of any object of interest, such as a suitcase or other container. It is particularly well-suited for surfaces that are generally smooth, and can be used on, for example, exterior surfaces of cars, trucks or other vessels.

Due to the simplicity and lightness of the device 10, it can readily and quickly be run around the exterior surfaces of objects of interest. After being run over all the surfaces of interest, it is placed in a frame holder 30, which will now be described in detail, for enabling samples to be analyzed in an IMS device.

The frame holder 30 is shown in detail in FIG. 3 and 4. The frame holder 30 comprises a base frame 32 and an upper frame 34. The base frame 32 is a simple rectangular frame, and includes an upwardly extending cylindrical peg 36 at a corner of the front and right hand edges thereof. A hinge connection 38 is provided generally along the right hand edge between the base and upper frames 32, 34. A vertical holding plate 40 is secured along this hinge connection 38.

The base frame 34, as shown in FIG. 3, has a circular hole 62. The hole 62 is located at the corner of a generally L-shaped shallow recess 64. A vertical lip 66 extends along the rear of the base frame 32.

The upper frame 34 generally corresponds to the lower or base frame 32 and is pivotally connected by the hinge connection 38. The upper frame 34 has a rectangular recess 42 in its top surface as shown in FIG. 4. It further has a circular opening 44, aligned with the hole 62 in the base frame 32, which opening 44 is provided with an annular sealing member 46. The upper frame 34 additionally includes a clip 48 for engaging the cylindrical peg 36.

With reference to FIGS. 6(a) and 6(b), the upper frame 34 includes a rectangular floating element 68, which as shown is machined from metal to provide vertical side edges 70, defining the rectangular recess 42. Within the recess 42, there is an annular portion 72i of further reduced thickness, including the circular opening 44, located coaxially therein. The opening 44 is defined by a pair of annular elements 74, 75, which are formed from a suitable plastic material and secured to the floating element 68, as shown in FIGS. 6(a) and 6(b).

The element 68 has, projecting from the side edges 70, pins 78, which are located within recesses or openings 80 of the upper frame 34, to enable the element 68 to float vertically, and laterally to a certain extent.

As shown in FIG. 3, to load a bag or collection device 10 onto the frame holder 30, the holder 30 is opened so that the clip 48 engages the peg 36 to hold the upper frame 34 open. The collection device or bag 10 is then placed on the base frame 32 inverted so that the bottom layer 12, with the sample on its outer surface, is visible, as in FIG. 4.

The upper frame 34 is then disengaged from the peg 36 and pivoted down to the closed configuration of FIG. 5. As shown in FIG. 6(a), without the collection bag 10 present, the floating element 68 naturally falls to a lower limit under the action of gravity. As shown in FIG. 6(b), with the collection bag 10 present, the floating element 68 is lifted and sandwiches the bag 10 against the base frame 32.

Turning to FIGS. 7 and 8, these show an IMS device, which can be a conventional Ion Mobility Spectrometer 50 as manufactured by Barringer Research Limited of Rexdale, Ontario. While an IMS device is shown, it will be appreciated that the present invention is applicable to any other suitable analysis device. The IMS device 50 has an input station 52 for inputting a sample, which is shown in greater detail in FIGS. 8(a) and 8(b).

The input station 52 has a pair of outwardly extending brackets 54 with cylindrical side bars 56 extending therebetween. A moveable support 58 is slidably mounted on the side bars 56. The frame holder 30 is dimensioned to fit on the movable support 58. Above the movable support 58 there is an inlet 60 for sample vapor.

As shown in FIG. 8(a), the movable support is first located at an extreme right hand position. The frame holder 30, containing the bag or collection device 10, as in FIG. 5 is then placed on the movable support 58. The support 58 and frame 30 are then moved to the left, to the position as shown in FIG. 8(b), where the vertical plate 40 abuts the side of the inlet 60.

In known manner, the IMS device 50 is then operated to desorb the sample. It can include a mechanism to that provides a heater and gas source, which is pressed up against the base frame 32, to further sandwich and seal the collection bag 10 in position. This involves heating the collection device 10 in the frame holder 30, so as to cause vaporization and desorption of any sample vapors. Simultaneously, a carrier gas is passed through the collection device 10, through the circular opening 44. It can be noted that this opening 44 and circular hole 62 align! generally with the aperture 22, to enable the carrier gas to pass freely through the bottom layer 12 and entrain sample vapors, for passing into the inlet 60. As the bag 10 was inverted before being placed on the frame holder 30, the layer 12 is now at the top and desorbed vapors do not have to pass through the other layer 14.

The sample vapors are then analyzed in the IMS device in known manner, and an appropriate reading taken.

The desorption or cleaning temperatures can be such as to cause slight charring of the fabric of the collection device 10, when formed from cotton. This is not considered to be significant. Indeed, after desorption, the device 10 can be subjected to a higher temperature to ensure that all volatile components are driven off from the collection device 10, so that it is clean and ready for reuse, without danger that residue from a previous sample may contaminate a later sample.

I claim:

1. A flexible, generally sheet-form collection device for use in collecting a sample for analysis, the collection device comprising top and bottom layers of a flexible material, and means securing the top and bottom layers together around substantially three sides thereof, with a fourth side of the collection device being open for insertion of a user's fingers, wherein both of the top and bottom layers are generally rectangular and are secured together along the sides and rear edges thereof, with the device being open along a front edge thereof, and wherein the bottom layer extends beyond the top layer along the front edge thereof.

2. A collection device as claimed in claim 1, wherein the top and bottom layers are formed from the same material and are continuous with one another at the rear edge, with the top and bottom layers being sewn together along the side edges.

3. A collection device as claimed in claim 2, wherein the top layer includes a circular aperture, to facilitate passage of vapor from a sample on the bottom layer.

4. A collection device as claimed in claim in 1, wherein the top layer comprises an open mesh, providing for free passage of gas and vapor, secured along rear and side edges to the bottom layer.

5. A collection device as claimed in claim 3 or 4, which is dimensioned to fit onto two fingers of a user's hand.

6. A collection device as claimed in claim 3 or 4, wherein at least the bottom layer is formed from cotton.

* * * * *